(12) United States Patent
Soltz et al.

(10) Patent No.: US 7,704,247 B2
(45) Date of Patent: Apr. 27, 2010

(54) DUAL FIBER-OPTIC SURGICAL APPARATUS

(76) Inventors: Barbara Ann Soltz, 81 Pine Brook Rd., Spring Valley, NY (US) 10977; Robert Soltz, 81 Pine Brook Rd., Spring Valley, NY (US) 10977; Michael Andrew Soltz, 81 Pine Brook Rd., Spring Valley, NY (US) 10977

( * ) Notice: Subject to any disclaimer, the term of this patent is extended or adjusted under 35 U.S.C. 154(b) by 1334 days.

(21) Appl. No.: 10/778,663

(22) Filed: Feb. 13, 2004

(65) Prior Publication Data

US 2004/0162490 A1 Aug. 19, 2004

Related U.S. Application Data

(60) Provisional application No. 60/447,068, filed on Feb. 13, 2003.

(51) Int. Cl.
*A61B 18/18* (2006.01)
(52) U.S. Cl. .................... 606/13; 606/8; 606/16
(58) Field of Classification Search ............. 606/3–17, 606/22; 607/88, 89, 104, 107; 600/104, 600/108, 473, 478
See application file for complete search history.

(56) References Cited

U.S. PATENT DOCUMENTS

| | | | | |
|---|---|---|---|---|
| 4,266,549 A | * | 5/1981 | Kimura | 606/3 |
| 4,862,886 A | * | 9/1989 | Clarke et al. | 600/473 |
| 5,192,278 A | * | 3/1993 | Hayes et al. | 607/105 |
| 5,303,026 A | * | 4/1994 | Strobl et al. | 356/318 |
| 5,419,312 A | * | 5/1995 | Arenberg et al. | 600/108 |
| 5,423,320 A | * | 6/1995 | Salzman et al. | 600/113 |
| 5,445,608 A | * | 8/1995 | Chen et al. | 606/12 |
| 5,582,190 A | * | 12/1996 | Slavin et al. | 128/898 |
| 6,063,093 A | * | 5/2000 | Winston et al. | 604/20 |
| 6,160,943 A | * | 12/2000 | Davis et al. | 385/126 |
| 6,221,068 B1 | * | 4/2001 | Fried et al. | 606/8 |
| 6,527,764 B1 | * | 3/2003 | Neuberger et al. | 606/10 |
| 6,551,346 B2 | * | 4/2003 | Crossley | 607/88 |
| 6,942,657 B2 | * | 9/2005 | Sinofsky et al. | 606/15 |
| 6,966,906 B2 | * | 11/2005 | Brown | 606/15 |

* cited by examiner

*Primary Examiner*—Ahmed M Farah

(57) ABSTRACT

Consistent with the present invention, a tube is provided that contains both a sensing and a laser delivery fiber to the target area. The length of the tube can be varied to any desired length. The end portion of the tube includes a second piece, which is a cap having two through holes or passages. These holes can be formed by standard machining or micromaching methods. The first hole can accommodate the sensing fiber, while the second hole contains the laser delivery fiber. The first and second holes extend in first and second directions, respectively, and form an angle therebetween such that the sensor fiber viewing area is within the radiation area created by the laser delivery fiber. Accordingly, the sensor fiber receives energy emitted from a central portion of the radiation area so that the temperature of the exposed tissue can be accurately determined.

20 Claims, 3 Drawing Sheets

# DUAL FIBER-OPTIC SURGICAL APPARATUS

Pursuant to 35 U.S.C. §119(e), the present application claims the benefit of provisional application Ser. No. 60/447,068, filed Feb. 13, 2003 and incorporated by reference herein.

The present invention is directed toward a surgical apparatus. In particular, the present invention relates to an apparatus suitable for tissue welding and other laser surgery applications.

Laser surgery has been selected as an alternative to conventional surgical methods for many years because of the potential for less physical trauma and injury to adjacent tissue, improved speed of the procedure and closure, improved healing rates and reduced scaring. The use of lasers for minimally invasive surgery (MIS) has been limited by a means to stabilize laser output, to automatically power down the laser at an endpoint and to prevent overheating of adjacent tissue, which can cause cell necrosis. These limitations are especially crucial in the development of reliable surgical methods to join or bond tissue using laser tissue welding techniques. For example, precise temperature control at the weld site is critical to effectively crosslink tissue to a solder or sealant biomaterial with strengths comparable to conventional closure methods such as staples or sutures.

BRIEF DESCRIPTION OF THE DRAWING

The present invention will become more fully understood from the detailed description given hereinbelow and the accompanying drawings which are given by way of illustration only, and thus are not limitative of the present invention, and wherein.

DETAILED DESCRIPTION OF PREFERRED EMBODIMENTS

Consistent with the present invention, a device has been designed and fabricated for use in laser surgery applications, such as laparoscopic procedures, and is suitable for other procedures where small size tools and functionality may be required. A surgical apparatus consistent with the present invention can contain two fiberoptic elements including a fiber that delivers laser energy to a tissue site and another fiber which collects radiation emitted from the tissue by virtue of its temperature. This collected emission is transmitted to a sensor, which may be incorporated into a feedback system for controlling, for example, laser energy applied to the tissue site and thus the temperature at the tissue site. The surgical apparatus can be passed through a tube or a cannula of a conventional trocar of a specific diameter (either 3, 5 or 8 mm diameter) without interfering with the normal function of the system, and may be comprised of two pieces or can be fabricated as one integral device.

In one example of this invention, the device includes a tube, cannula or elongated member containing both a sensing and a laser delivery fiber supplying laser energy to the target area. The length of the tube can be varied to any desired length. The end portion of the tube includes a second piece, which is a cap having two through holes or passages. These holes can be formed by standard machining or micromaching methods. The first hole can accommodate the sensing fiber, while the second hole contains the laser delivery fiber. The first and second holes extend in first and second directions, respectively, and form an angle therebetween such that the sensor fiber viewing area is within the radiation area created by the laser delivery fiber. The sensor fiber has is viewing area directed toward a central region of the exposure area, and thus receives energy emitted from the central portion of the irradiated area. Accordingly, the temperature of the exposed tissue can be accurately determined.

The following detailed description of the invention refers to the accompanying drawings. The same reference numbers in different drawings identify the same or similar elements. Also, the following detailed description does not limit the invention. Instead, the scope of the invention is defined by the appended claims and equivalents thereof.

Figure 1:
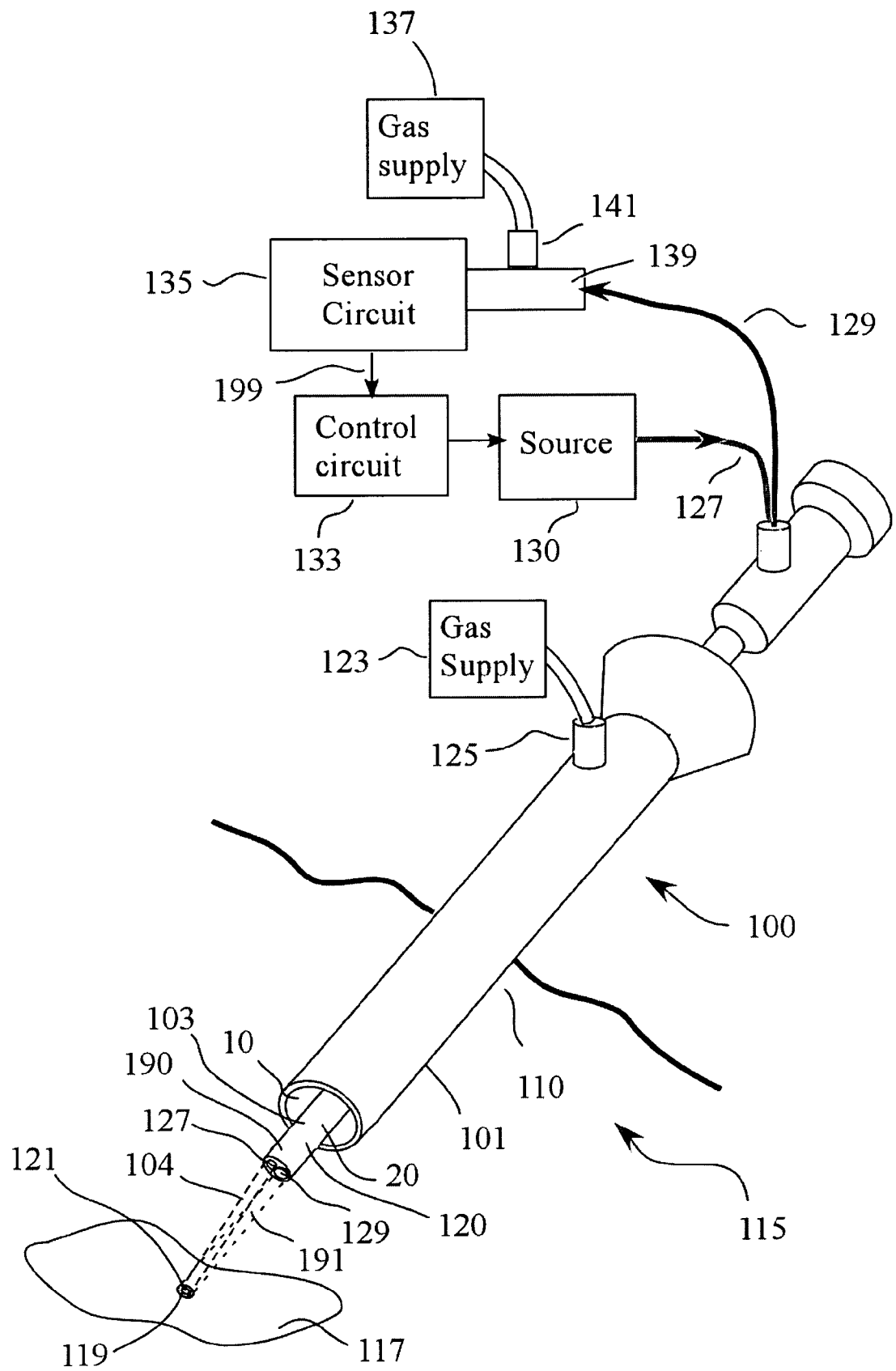
FIG. 1 illustrates a perspective view of a surgical apparatus in accordance with an aspect of the present invention.

FIG. 1 illustrates a perspective view of a surgical apparatus 100 consistent with the present invention. Surgical apparatus 100 includes a handpiece 120 which can be held by a user or provided within a portion of trocar 110 such as an elongated member, tube or cannula 101. Handpiece 120 includes a tube, cannula or elongated member 103 and optical fibers 127 and 129 that extend through elongated member 103. An optical source 130, such as a laser and preferably a semiconductor laser, is coupled to optical fiber 127 and provides optical radiation at a desired wavelength to fiber 127. The radiation is typically light having a wavelength in a range of 1402 nm-1420 nm. Fiber 127 is typically a conventional low OH⁻ optical fiber introducing relatively little loss to optical signals supplied thereto. The optical radiation propagates through fiber 127, and exits fiber 127 at end portion 190 of elongated member 103.

In laproscopic applications, end portion 190 is inserted into a body cavity 115, and the optical radiation output from fiber 127 exposes tissue 117 over an exposure area 119 along dotted lines 104. A tissue adhesive, as described for example, in U.S. patent application Ser. No. 09/973,332, filed Oct. 9, 2001, incorporated by reference herein, may be applied to tissue 117 prior to exposure. In response to such exposure, optical energy emanates from tissue exposure area 119. A portion of the optical energy is received by a known optical fiber 129, which is typically a hollow core optical fiber. As discussed in greater detail below, optical fiber 129 is positioned in a direction indicated by dotted lines 191 in order to receive optical energy emanating from a central region 121 of exposure area 119.

Fiber 129 typically has a diameter of 3 mm and an inner diameter of 2 mm to receive a relatively large amount of optical energy. Fibers having smaller inner diameters may be used having greater flexibility, but will not transmit as much light or optical energy. It is noted that that amount of light or optical energy received by and propagating through fiber 129 varies with the cube of the diameter of the hollow core.

Typically, the optical energy or light emanating from tissue 117 is sensed by sensor circuit 135 at one or more wavelengths within a range of 7-15 microns. Other sensors can be used to detect light, optical energy or radiation at other wavelengths. The optical energy travels through 129 and through adapter 139 to sensor circuit 135. In response to the received optical energy, the sensor circuit generates a sense signal 199, which is typically indicative of a temperature of central region 121 and supplied to control circuit 133. Optical source 130 is coupled to control circuit 133, and is controlled by the control circuit in response to sense signal 199.

Figure 2:
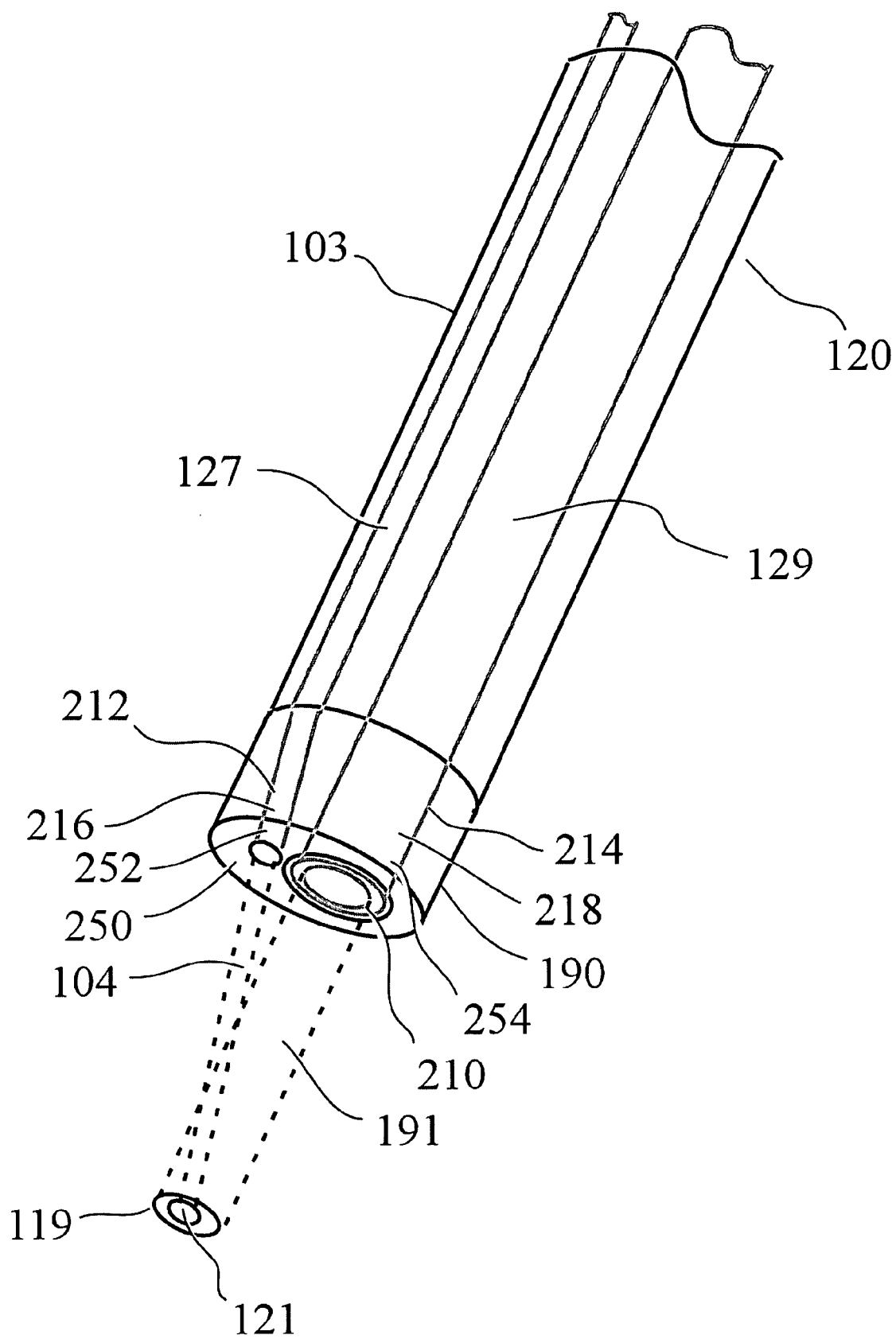
FIG. 2 illustrates is a detailed perspective view of a surgical apparatus consistent with a further aspect of the present invention.

Handpiece 120 and optical fibers 127 and 129 are shown in greater detail in FIG. 2. Optical fiber 129 has a hollow core 210 through which optical energy received from a central region 121 of exposure area 119 propagates to sensor circuit 135. End portions 216 and 218 of fibers 127 and 129, respectively, are provided in corresponding passages 212 and 214 of end portion 190 of elongated member 103. Passages 212 and 214 are oriented along directions indicated by dashed lines 104 and 191, and fibers 127 and 129 are secured within passages 212 and 214 by either friction fit or an adhesive, such as cyanoacrylate. The directions form an angle, as shown in greater detail in FIGS. 3(*a*) and 3(*b*).

Typically, fiber end portions 216 and 218 are provided at about one inch away from exposure area 117. Accordingly, the angle is preferably selected such that end portion 218 of fiber 129 receives optical energy from central region 121 of exposure area 117 at the one inch distance. By receiving and transmitting optical energy from central region 121 to sensor circuit 135, a sense signal which accurately reflects the temperature of central region 121 can be obtained.

As shown in FIG. 2 fiber end portions 216 and 218 are flush with outer surface 250 of end portion 190 of elongated member 103. Consistent with a further aspect of the present invention, however, both end portions may be recessed to positions 252 and 254 from outer surface 250.

Figure 3A:
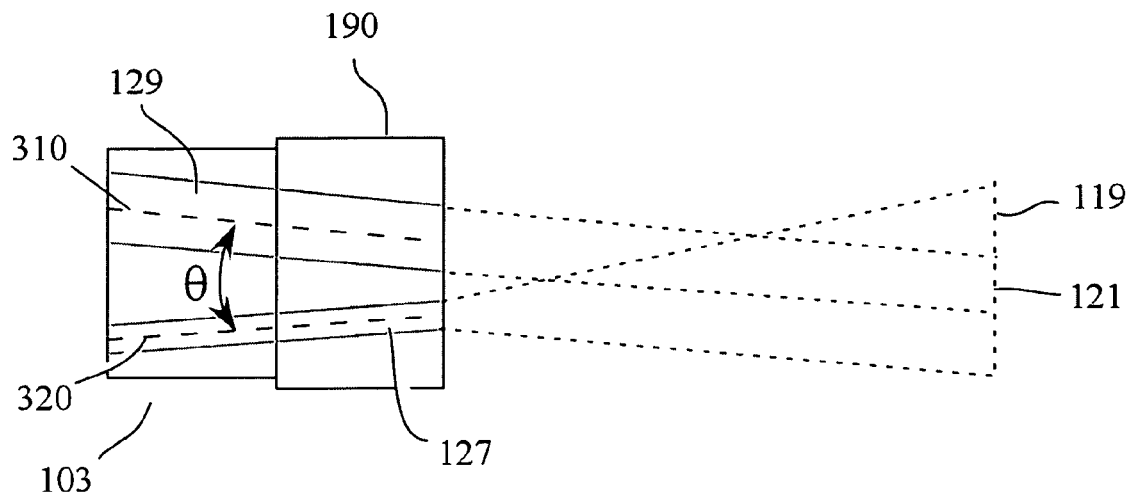
FIGS. 3(a) and 3(b) illustrate cross-sectional views of alternative embodiments of the present invention.
Figure 3B:
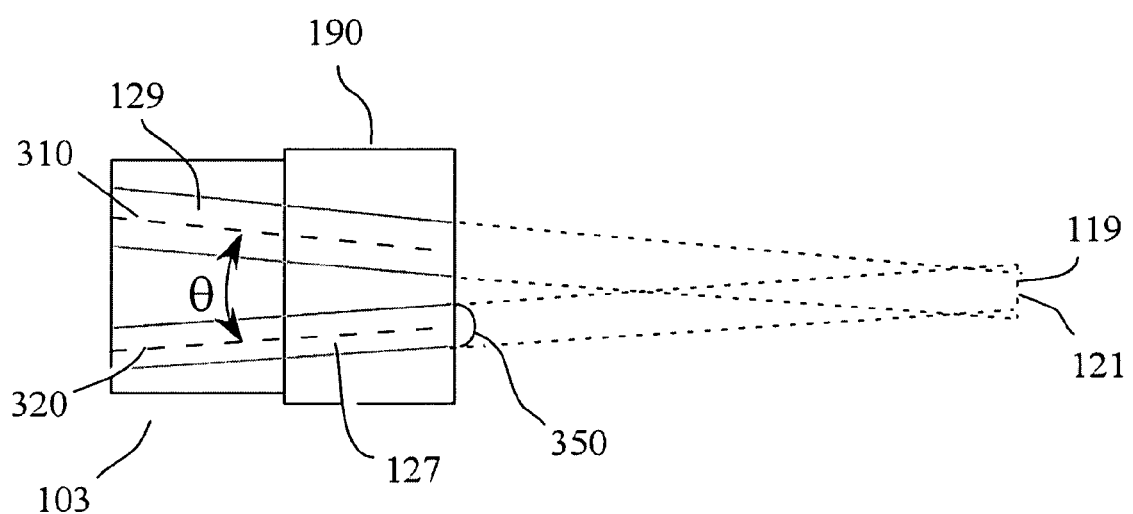

FIGS. 3(*a*) and 3(*b*) illustrate cross-sectional views of alternative embodiments of the present invention. In FIG. 3(*a*), light emitted from fiber 127 diverges and exposes a larger area 119. In FIG. 3(*b*), collimating lens 350 may be provided to collimate the optical radiation or light output from fiber 127 to thereby provide a beam that does not diverge substantially, and has substantially uniform power density over the exposure area. Collimated exposure area thus has a more uniform power density or intensity than without collimation. Accordingly, even if fiber end portion 218 of fiber 129 is not located at an optimal distance away from exposure area 119 and receives light or radiation not from the central portion of the exposure area, an adequate amount of light or radiation can nonetheless be detected and accurate temperature control can be achieved.

In both FIGS. 3(*a*) and 3(*b*), central axes 310 and 320 of fibers 129 and 127, respectively, extend parallel to directions of passages 212 and 214. Axes 310 and 320 form an angle θ such that fiber end portion 218 is typically directed toward and receives optical energy from central region 121, as noted above.

Returning to FIG. 1, optional gas supplies 137 and 123 can be provided to supply purging gas, typically carbon dioxide through hollow core 210 and through elongated member 101 to flush moisture, debris, gases and other contaminants released in response to tissue exposure and heating. In particular, gas supply 137 can be provided to a pressure fitting 141 of adapter 139 to provide a purging gas flow down hollow core 210 of fiber 129. Such purging gas flow advantageously creates a positive pressure to prevent tissue originating contaminants from interfering or blocking the received optical energy impinging on fiber end portion 218. In addition, gas supply 123 can supply purging gas flow through fitting or valve 125 into a space separating inner surface 10 of elongated member 101 and outer surface 20 of elongated member 103 to further flush such contaminants away from fiber end portion 218, as well as fiber end portion 216.

While the foregoing invention has been described in terms of the embodiments discussed above, numerous variations are possible. For example, although elongated endpiece 190 and elongated member 120 have described above as having a unitary construction, endpiece 190 may be a separate unit, joined to elongated member 120 by a friction fit. Endpiece 190 may then be detached and discarded after a procedure and replaced with another endpiece, advantageously eliminating the need to clean or sterilize the endpiece after each use. Accordingly, modifications and changes such as those suggested above, but not limited thereto, are considered to be within the scope of the following claims.

The invention claimed is:

1. A surgical apparatus, comprising:
   an elongated member having a distal end portion, the elongated member having first and second passages that extend through the distal end portion, the first passage extending in a first direction and the second passage extending in a second direction that intersects the first direction at a location beyond the first and second passages to form an angle; and
   first and second optical fibers, a portion of the first optical fiber being provided in the first passage and a portion of the second optical fiber being provided in the second passage,
   wherein said first optical fiber is configured to carry optical radiation, said optical radiation exposing a tissue over an exposure area, said second optical fiber being configured to receive a portion of optical energy emitted from said exposure area of said tissue, and
   wherein said second optical fiber has a hollow core configured to provide a gas flow.

2. A surgical apparatus in accordance with claim 1, wherein said portion of optical energy is emitted from a central region of said exposure area of said tissue.

3. A surgical apparatus in accordance with claim 1, wherein said elongated member is a first elongated member, said apparatus further comprising:
   a second elongated member, said first elongated member being provided within said second elongated member.

4. A surgical apparatus in accordance with claim 3, wherein said second elongated member is a cannula.

5. A surgical apparatus in accordance with claim 1, further comprising:
   an optical source coupled to said first optical fiber and being configured to provide said optical radiation to said first optical fiber; and
   an optical sensor circuit coupled to said second optical fiber and being configured to receive said optical energy from said second optical fiber.

6. A surgical apparatus in accordance with claim 5, wherein said optical sensor circuit is configured to generate a control signal in response to said optical energy, said surgical apparatus further comprising a control circuit coupled to said optical sensor circuit and said optical source, said control circuit being configured to adjust an output power of said optical source in response to said control signal.

7. A surgical apparatus in accordance with claim 6, wherein said control signal is indicative of a temperature of said tissue.

8. A surgical apparatus in accordance with claim 5, wherein said optical source is a laser and said optical radiation is at wavelength of 1402 nm-1420 nm.

9. A surgical apparatus in accordance with claim 1, wherein said distal end portion has an outer surface, a first fiber end portion of said first optical fiber and a second fiber end portion of said second optical fiber being recessed from said outer surface of said distal end portion.

10. A surgical apparatus in accordance with claim 1, further comprising a collimating lens coupled to said first optical fiber to thereby collimate said optical radiation.

11. A surgical apparatus in accordance with claim 1, further comprising a gas supply configured to provide a gas flow through said hollow core.

12. A surgical apparatus in accordance with claim 1, wherein the distal end portion of the elongated member is detachable from a remaining portion of the elongated member.

13. A surgical apparatus, comprising:

a first elongated member;

a second elongated member provided in said first elongated member, said second elongated member having a distal end portion; and first and second optical fibers provided in said second elongated member, said first optical fiber being configured to supply optical radiation to a tissue over an exposure region, said distal end portion of said second elongated member having a first passage for accommodating said first optical fiber and a second passage for accommodating said second optical fiber, the first and second passages extend in first and second directions, respectively, that intersect one another at a location beyond the second elongated member, such that a fiber end portion of said second optical fiber is directed toward said exposure region and said second optical fiber receives a portion of optical energy emitted from said exposure region in response to said optical radiation, and wherein said second optical fiber further has a hollow core configured to supply a gas flow.

14. A surgical apparatus in accordance with claim 13, wherein said portion of said optical energy is emitted from a central portion of said exposure region.

15. A surgical apparatus in accordance with claim 13, wherein said first elongated member is a cannula.

16. A surgical apparatus in accordance with claim 13, further comprising an optical source generating said optical radiation and a sensor configured to receive said portion of said optical energy.

17. A surgical apparatus in accordance with 13, further comprising a collimating lens coupled to a fiber end portion of said first optical fiber, said collimating lens being configured to collimate said optical radiation supplied to said tissue.

18. A surgical apparatus in accordance with claim 13, further comprising a gas source supplying a gas flow through said hollow core.

19. A surgical apparatus in accordance with claim 13, wherein an inner surface of said first elongated member is separated by an outer surface of said second elongated member, said surgical apparatus further comprising a gas source supplying a gas flow into a region between said inner surface of said first elongated member and said outer surface of said second elongated member.

20. A surgical apparatus in accordance with claim 13, wherein the distal end portion of the second elongated member is detachable from a remaining portion of the second elongated member.

* * * * *